(12) United States Patent
Shi et al.

(10) Patent No.: US 8,524,158 B2
(45) Date of Patent: Sep. 3, 2013

(54) WEARABLE CHEMICAL DISPENSER WITH USEFUL LIFE INDICATOR

(75) Inventors: Deliang Shi, Racine, WI (US); Steven B. Mineau, Racine, WI (US); Sean P. Kingston, Oak Creek, WI (US); Dirk K. Nickel, Mukwonago, WI (US); Neil P. Williams, Racine, WI (US); Kimberly Kristopeit, Union Grove, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 348 days.

(21) Appl. No.: 13/105,592

(22) Filed: May 11, 2011

(65) Prior Publication Data
US 2012/0288414 A1   Nov. 15, 2012

(51) Int. Cl.
*A61L 9/12* (2006.01)

(52) U.S. Cl.
USPC ............... 422/124; 422/5; 239/55; 239/58

(58) Field of Classification Search
USPC ............... 422/5, 123, 124, 125; 239/55, 58, 239/59
See application file for complete search history.

(56) References Cited

U.S. PATENT DOCUMENTS

| | | |
|---|---|---|
| 4,062,649 A | 12/1977 | Kuderna et al. |
| 4,293,095 A | 10/1981 | Hamilton et al. |
| 4,301,095 A | 11/1981 | Mettler et al. |
| 4,824,827 A | 4/1989 | Kelly et al. |
| 5,111,477 A | 5/1992 | Muderlak |
| 5,293,648 A | 3/1994 | Finley |
| 5,647,052 A | 7/1997 | Patel et al. |
| 6,050,551 A | 4/2000 | Anderson |
| 6,371,450 B1 | 4/2002 | Davis et al. |
| 6,582,714 B1 | 6/2003 | Emmrich et al. |
| 6,592,828 B2 | 7/2003 | Munoz |
| 6,663,838 B1 | 12/2003 | Soller et al. |
| 6,722,578 B2 | 4/2004 | Skalitzky et al. |
| 6,790,670 B2 | 9/2004 | Munagavalasa et al. |
| 6,926,902 B2 | 8/2005 | Inoue et al. |
| 7,007,861 B2 | 3/2006 | Ketcha et al. |
| 7,008,180 B2 | 3/2006 | Fujimori et al. |
| 7,152,809 B2 | 12/2006 | Ketcha et al. |
| 7,164,849 B1 | 1/2007 | Bankers et al. |
| 7,168,630 B1 | 1/2007 | Ketcha et al. |
| 7,175,815 B2 | 2/2007 | Yamasaki et al. |
| 7,188,780 B2 | 3/2007 | Martens, III |
| 7,213,770 B2 | 5/2007 | Martens, III et al. |

(Continued)

FOREIGN PATENT DOCUMENTS

| | | |
|---|---|---|
| WO | 9846280 | 10/1998 |
| WO | 0165931 | 9/2001 |

(Continued)

OTHER PUBLICATIONS

PCT/US2012-036305 International Search Report dated Sep. 13, 2012.

*Primary Examiner* — Sean E Conley

(57) ABSTRACT

Wearable devices for dispensing insect repellents, fragrances, and/or other chemicals along the outside of the clothing of a human are disclosed. The devices are of the type that are clipped onto a belt or the like, and use a powered fan to dispense active. Air flow is directed through a substrate and adjacent to a useful life indicator to improve reliability of the useful life indicator.

22 Claims, 6 Drawing Sheets

(56) References Cited

U.S. PATENT DOCUMENTS

| | | |
|---|---|---|
| 7,285,248 B2 | 10/2007 | Yamamoto et al. |
| 7,440,683 B2 | 10/2008 | Bankers et al. |
| 7,597,857 B2 | 10/2009 | Reece |
| 7,670,566 B2 | 3/2010 | Adair et al. |
| 2002/0062593 A1 | 5/2002 | Matsunaga et al. |
| 2003/0044326 A1 | 3/2003 | Yamasaki et al. |
| 2003/0160062 A1 | 8/2003 | Inoue et al. |
| 2003/0175171 A1 | 9/2003 | Yamamoto et al. |
| 2005/0019165 A1 | 1/2005 | Fujimori et al. |
| 2005/0079113 A1 | 4/2005 | Selander |
| 2005/0226788 A1 | 10/2005 | Hrybyk et al. |
| 2006/0039835 A1 | 2/2006 | Nottingham et al. |
| 2006/0137241 A1 | 6/2006 | Yamasaki et al. |
| 2007/0036688 A1 | 2/2007 | Hayes-Pankhurst et al. |
| 2007/0058955 A1 | 3/2007 | Bankers et al. |
| 2007/0058956 A1 | 3/2007 | Bankers et al. |
| 2007/0087679 A1 | 4/2007 | Yamasaki et al. |
| 2007/0111654 A1 | 5/2007 | Yamasaki et al. |
| 2007/0183932 A1 | 8/2007 | Adair et al. |
| 2007/0183940 A1 | 8/2007 | Yamamoto et al. |
| 2007/0258865 A1 | 11/2007 | Yamasaki et al. |
| 2008/0056691 A1* | 3/2008 | Wingo et al. ............ 392/395 |
| 2008/0141928 A1 | 6/2008 | Adair et al. |
| 2009/0008411 A1 | 1/2009 | Schumacher et al. |
| 2009/0060799 A1 | 3/2009 | Torres |
| 2010/0132246 A1 | 6/2010 | Ohtsuka et al. |
| 2011/0038761 A1 | 2/2011 | Saleh et al. |

FOREIGN PATENT DOCUMENTS

| | | |
|---|---|---|
| WO | 02060246 | 8/2002 |
| WO | 03080131 | 10/2003 |
| WO | 2004089076 | 10/2004 |
| WO | 2005063013 | 7/2005 |
| WO | 2006011429 | 2/2006 |
| WO | 2007033182 | 3/2007 |
| WO | 2007086307 | 8/2007 |
| WO | 2008132969 | 11/2008 |
| WO | 2009031891 | 3/2009 |
| WO | 2009053399 | 4/2009 |
| WO | 2009118476 | 10/2009 |

* cited by examiner

WEARABLE CHEMICAL DISPENSER WITH USEFUL LIFE INDICATOR

CROSS-REFERENCES TO RELATED APPLICATIONS

Not Applicable.

STATEMENT REGARDING FEDERALLY SPONSORED RESEARCH

Not Applicable.

BACKGROUND OF THE INVENTION

1. Field of the Invention

This invention relates to wearable devices that dispense chemicals such as insect repellents and/or fragrances.

2. Description of the Related Art

Various techniques have been developed to provide humans with protection from insect bites. For insect control inside buildings a primary emphasis is placed on trying to keep insects from entering the building at all (e.g. placing screens over windows). This sometimes is supplemented with chemical treatment of room air and/or the use of traps. See e.g. U.S. Pat. Nos. 6,582,714 and 7,175,815, and also U.S. Patent Application Publications 2005/0079113, 2006/0039835, 2006/0137241, and 2007/0036688.

When the individual is outdoors where the area cannot be effectively screened, and the individual is mostly staying in a particular area (e.g. at a picnic, or on a patio near a building), traps and repellents are the primary focus.

Alternatively, when the individual is moving away from a single area that they control, individuals often apply a personal insect repellent to clothing or directly to their skin. However, some consumers have expressed a reluctance to apply insect repellents directly to their skin or to delicate clothing.

As a result, portable electrical devices having a fan and an insecticide source have been developed. These devices may have a clip so that they can easily be mounted on a belt, a purse, or even a pocket, and thus be "worn" by the consumer as they move outside. The device may draw air through, or blow air past, a substrate impregnated with an insect repellent or other air treatment chemical, thereby dispensing the active into the air, preferably (in the case of a repellent) downward along the outside of a human's clothing. See U.S. Pat. Nos. 6,296,902, 7,007,861, 7,152,809, and 7,168,630, and U.S. Patent Application Publication Nos. 2003/0175171, 2003/0175171, 2007/0183940, 2009/0008411, and 2009/0060799.

However, some such devices may blow the active too far out away from the human body, causing too little of the active to reach locations of primary concern (e.g. near ankles). Other such devices do not provide a way of minimizing waste of the active, such as while blower operation is suspended between uses. Still other such devices are unduly costly, are too heavy or have other deficiencies.

There have even been a variety of attempts to develop use indicators associated with air treatment devices, so that consumers can tell when the device needs servicing/refilling. See U.S. Pat. Nos. 4,062,649, 4,293,095, 4,824,827, 5,293,648, and U.S. Patent Application Publication No. 2008/0141928, which is incorporated herein by reference.

However, in some such devices the amount of air moving past the substrate does not correspond to the amount of air that flows past the useful life indicator. This could possibly cause the useful life indicator to indicate that the device is still effective after the insect repellent has been depleted.

Hence, a need exists for improved devices for dispensing insect control actives and other air treatment chemicals, particularly those that can operate without applying chemicals directly to the skin or clothing and more accurately display the useful life of the device.

In view of the advances in the art provided by the devices of U.S. Patent Application Publication Nos. 2008/0141928 and 2009/0008411 even further improvements to this technology would be beneficial to consumers.

SUMMARY OF THE INVENTION

The present invention provides a dispensing device for dispensing an air treatment chemical. In one aspect the invention provides a wearable device for dispensing an air treatment chemical, where the device has:

(a) a main housing unit including an inlet for permitting air to enter into an interior space of the housing, an outlet for permitting air mixed with an air treatment chemical to exit the interior space, a fan chamber, a guide chamber, and a slot between the fan chamber and the guide chamber;

(b) a cartridge positioned in the housing, the cartridge including a substrate bearing an air treatment chemical and a useful life indicator;

(c) a frame positioned in the housing, the frame having a throughhole adjacent to the guide chamber;

(d) a power supply mounted in the housing;

(e) a motor mounted in the housing, the motor being powered by the power supply; and (f) a fan mounted in the fan chamber, the fan being capable of moving air from the inlet adjacent to the substrate so as to mix air treatment chemical into the moving air, and then deliver a mixture of air and air treatment chemical through the outlet to an outside of the housing. The slot, guide chamber, and throughhole define a flow path for the moving air to flow adjacent to the useful life indicator.

In one form, the wearable device further includes a switch for turning the fan on and off. In another form, the useful life indicator changes appearance by evaporation of a material. In another form, the flow path directs the moving air under the useful life indicator. In another form, the frame further includes a sunken area between the slot and the fan chamber. In another form, the sunken area directs the moving air from the useful life indicator to the housing outlet.

In another form, the wearable device also includes a movable slide cover that blocks air flow when in a first, closed position and allows the air to flow when in a second, open position. The slide cover has a projection thereon that interacts with a switch so that moving the slide cover to the second, open position activates the switch to turn on the fan. In another form, the wearable device also includes a rotating activation button that must be rotated by interaction with the projection of the slide cover before the switch can be activated.

In another form, the rotating activation button, as it is rotated by interaction with the projection of the slide cover as the slide cover is moved, moves from a position inhibiting the evaporation of material from the useful life indicator to a second position wherein evaporation of material from the useful life indicator is readily permitted. In another form, the rotating activation button is located adjacent to the slot.

In another form, the fan chamber is defined by a vertical wall. In another form, the fan chamber and the guide chamber are separated by the vertical wall. In another form, the slot is located in the top edge of the vertical wall. In another form, the frame contacts a top edge of the vertical wall. In another form, a top of the guide chamber is defined by the frame. In another form, the throughhole defines a portion of the top of the guide chamber. In another form, the throughhole is the sole outlet for airflow from the guide chamber. In another form, the slot is the sole inlet for airflow into the guide chamber.

In another aspect, the invention provides a method of indicating a remaining amount of useful life of an air treatment chemical being dispensed by a wearable device. The method includes:

A. providing the wearable device having:

(i) a main housing unit including an inlet for permitting air to enter into an interior space of the housing, an outlet for permitting air mixed with an air treatment chemical to exit the interior space;

(ii) a cartridge positioned in the main housing unit, the cartridge including a substrate bearing an air treatment chemical and the useful life indicator;

(iii) a frame positioned in the main housing unit;

(iv) a power supply mounted in the main housing unit;

(v) a motor mounted in the main housing unit, the motor being powered by the power supply;

(vi) a fan capable of moving air from the inlet adjacent to the substrate so as to mix air treatment chemical into the moving air, and then deliver a mixture of air and air treatment chemical through the outlet to an outside of the main housing unit;

B. providing a flow path for the moving air to flow adjacent to the useful life indicator; and C. directing the moving air through the flow path at useful life indicator; wherein the moving air flows past the underside of the useful life indicator.

In one form, the main housing unit includes a fan chamber, a guide chamber, and a slot between the fan chamber and the guide chamber and the frame includes throughhole adjacent to the guide chamber. The fan chamber, guide chamber, slot, and throughhole define the flow path and the moving air flows along an underside of the useful life indicator.

These and other features, aspects, and advantages of the present invention will become better understood upon consideration of the following detailed description, drawings, and appended claims.

DETAILED DESCRIPTION OF THE INVENTION

Figure 1:
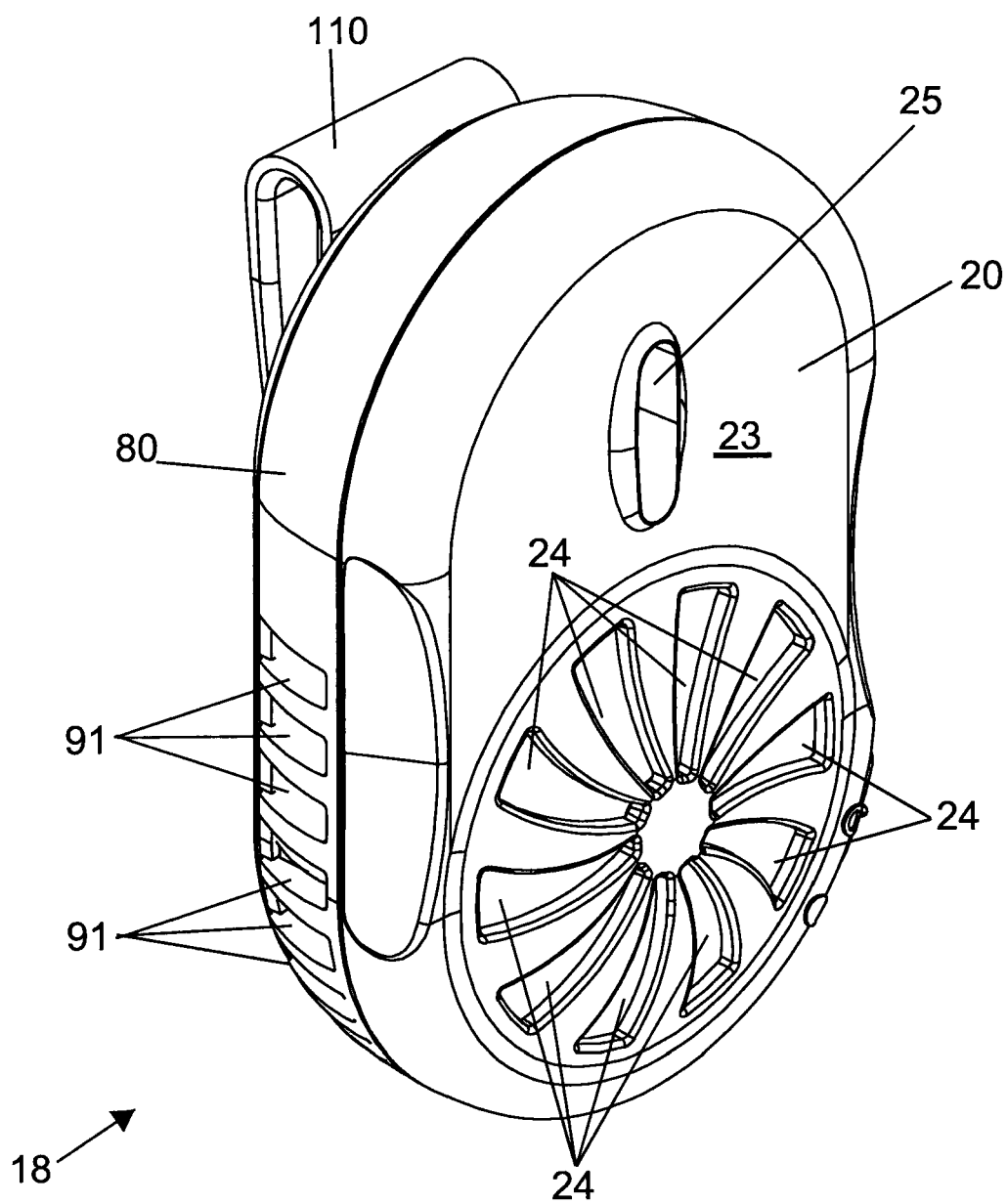
FIG. 1 is a left, top, frontal perspective view of a wearable device according to the invention.

An example wearable chemical dispenser 18 is shown in FIGS. 1-6. The wearable chemical dispenser 18 includes a top housing section 20 having a generally oblong side well 22 that extends from a top wall 23. In use, the wall 23 is typically frontally disposed and acts as a lid. A plurality of spaced apart apertures 24 are radially arranged in the top wall 23 of the top housing section 20. The apertures 24 provide an inlet for permitting air to enter into an interior space of the wearable chemical dispenser 18. A tab 26 provides a means to grasp the top housing section 20 when opening the top housing section 20.

The wearable chemical dispenser 18 also includes a slide cover 28 having an on-off button 29, openings 31, and a cam projection 32. A fastener 34 mounts the slide cover 28 to the top housing section 20 such that the slide cover 28 may rotate with respect to the top housing section 20 when a user moves the on-off button 29 along the side wall 22 of the top housing section 20. In the 'off' position, the slide cover 28 closes the apertures 24 that are radially arranged in the top wall 23 of the top housing section 20. In the 'on' position, the openings 31 of the slide cover 28 align with the apertures 24 that are radially arranged in the top wall 23 of the top housing section 20.

Figure 2:
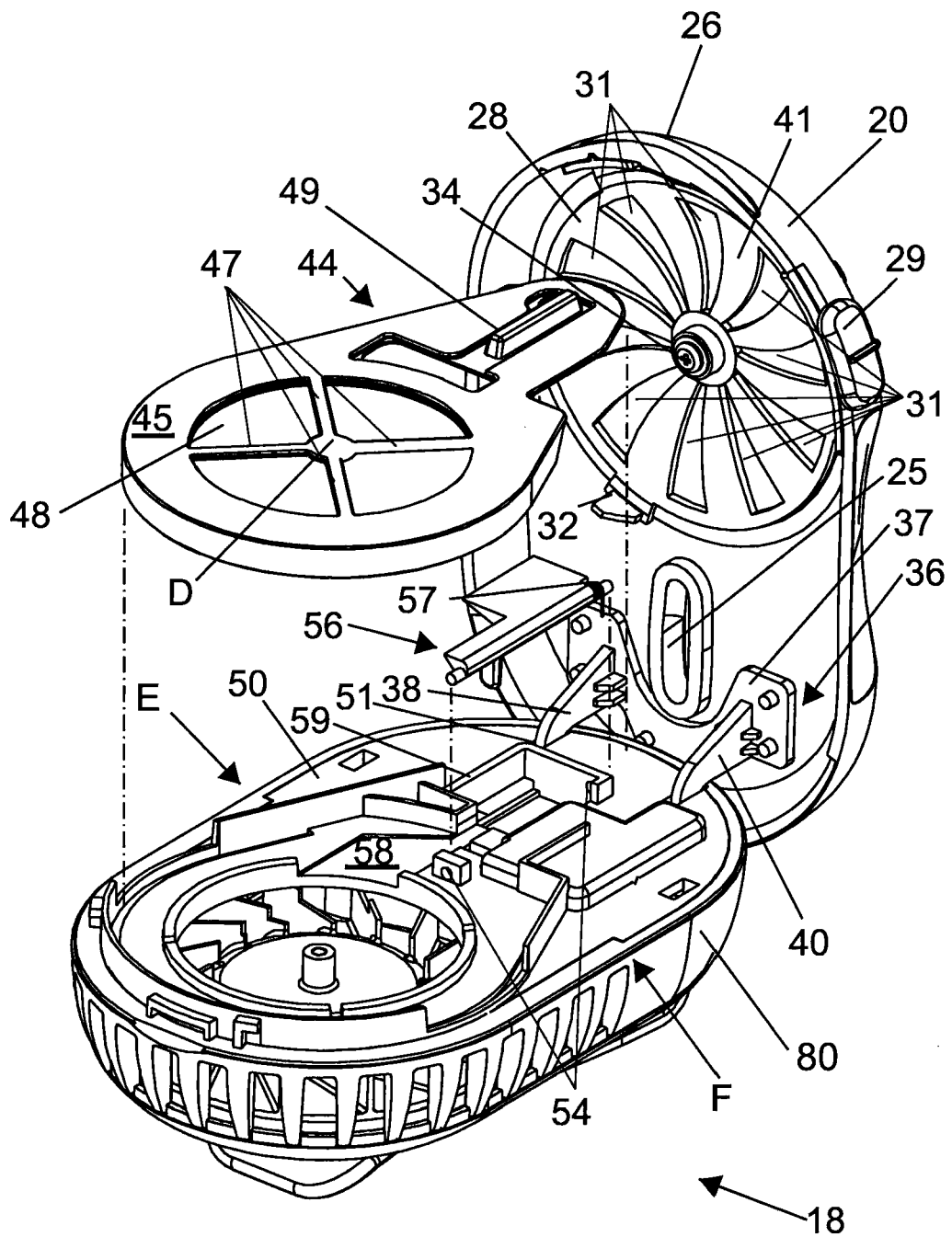
FIG. 2 is a right, bottom perspective view of the device of FIG. 1 with the front cover in an open position and the cartridge not yet installed.

The wearable chemical dispenser 18 also includes a hinge bracket 36 that is mounted to an inner surface of the top housing section 20 as shown in FIG. 2. The hinge bracket 36 has a flat base plate 37 that mounts to the top housing section 20, a generally L-shaped arm 38 having an inwardly directed pivot pin (not shown) at its end, and generally L-shaped arm 40 having an inwardly directed pivot pin (not shown) at its end. The arm 38 and the arm 40 are spaced apart on the plate 37 as shown in FIG. 2. The hinge bracket 36 forms part of a hinge mechanism as described below. The hinge mechanism allows a user to open the top housing section 20 to the open position of FIG. 2 so that a new refill cartridge 44 can be installed on the frame 50.

A replaceable refill cartridge 44 is provided with the wearable chemical dispenser 18. The refill cartridge 44 has a generally slab-like support structure 45. In top plan view, the refill cartridge 44 has an essentially tear-drop shaped overall appearance, with a generally circular portion at one end and a generally triangular portion at another end. There is a spoke support 47 across a circular opening 52 through the refill cartridge 44 (see FIG. 2). Across the spoke support 47 is positioned a fabric substrate 48. When air is drawn in, the air passes through the fabric substrate 48. The choice of the fabric, and its porosity, the speed of the air flow, and the vapor pressure of the active, are the main factors in coordinating the speed of use up of the active with the speed of use up of a visual useful life indicator 49 (see FIG. 2) that can be viewed through the slot 25 of the top housing section 20. An example refill cartridge has a twelve hour life, and the visual useful life indicator 49 is designed to evaporate or change in appearance after twelve hours. A suitable visual useful life indicator is described in U.S. Patent Application Publication No. 2008/0141928.

By impregnating the fabric substrate 48 with an appropriate air treatment chemical, air entering the device will pick up some of the volatile chemical, and dispense it out of the device. Active release rates of 0.2 milligrams per hour (mg./hr.) or higher are preferred. Particularly preferred actives are transfluthrin, prallethrin, vaporthrin, tefluthrin, and esbiothrin or other synthetic pyrethroids. For use in controlling mosquitoes, it is preferred to use metofluthrin from the Sumitomo Chemical Company (trade name SumiOne). The impregnation material can be pure active, or for ease of handling the material can be dissolved in a hydrocarbon or other solvent. Alternatively, or in addition, the fabric may also bear a fragrance, a deodorizer, or other air treatment chemical. It is preferred to have the fabric substrate 48 configured so that the pressure drop across the substrate is no more than 40 Pascals (Pa). Suitable fabrics can be made of woven or non-woven materials providing only minimal resistance to the airflow.

The fabric substrate 48 should also be capable of holding an air treatment chemical dosed onto the material and also allow ready migration of the active to the surface so as to allow its evaporation in response to the airflow. For an air treatment chemical that is hydrophobic and migrateable at common environmental temperatures between about 10° C. and 40° C. (e.g., metofluthrin), suitable materials include, only by way of example, polyester, polypropylene, cotton, cellulose, poly-rayon, and other similar fabrics. These can be nonwovens with basis weights ranging from 10 grams per square meter (gsm) to 40 grams per square meter (gsm), fabricated from synthetic, natural, or combined synthetic and natural polymeric materials.

The ideal fabric substrate 48 should also allow for wicking of the air treatment chemical following dosing so as to ensure efficient distribution throughout the substrate, and thereafter allow migration of the air treatment chemical to the substrate surface to replenish the air treatment chemical that is being evaporated by the passing airflow. Dosing may be by dropping, spraying, printing, or other conventional delivery of a liquid air treatment chemical to the substrate. A particularly desirable fabric is a non-woven felted material with a basis weight of 20-30 gsm fabricated from polyethylene terephthalate.

A frame 50 is located below the refill cartridge 44 in the wearable chemical dispenser 18. The frame 50 has a generally oblong perimeter, and supports the refill cartridge 44 (see FIG. 2). Note that one side of the essentially triangular portion of the refill cartridge 44 is straight and the other is indented. This slight lack of symmetry is designed to accommodate a corresponding slight lack of symmetry along the top side of frame 50, and to thereby prevent a consumer from installing the refill cartridge 44 inside-out on the frame 50. One end of the frame 50 has a pair of slots 51 that form part of a hinge mechanism as described below. A circular opening 52 is provided at the other end of the frame 50. Holes 54 in the frame 50 support a rotating activation button 56 that is biased by a rotary spring 57 into an off position. In the "off" position, the rotating activation button 56 abuts the exposed underside of the useful life indicator 49.

The frame 50 also includes a throughhole 55. The throughhole 55 is positioned below the rotating activation button 56 and the useful life indicator 49. The frame also includes a sunken area 58 and a vertical rib 59. The sunken area extends from the throughhole 55 to the circular opening 52 of the frame 50. The vertical rib 59 ensures that the refill is sealed and directs airflow toward the useful life indicator 49. The combination of the throughhole 55 and the sunken area 58 allows air to flow from a guide chamber 89 past the useful life indicator 49 and back to a fan chamber 83.

Figure 3:
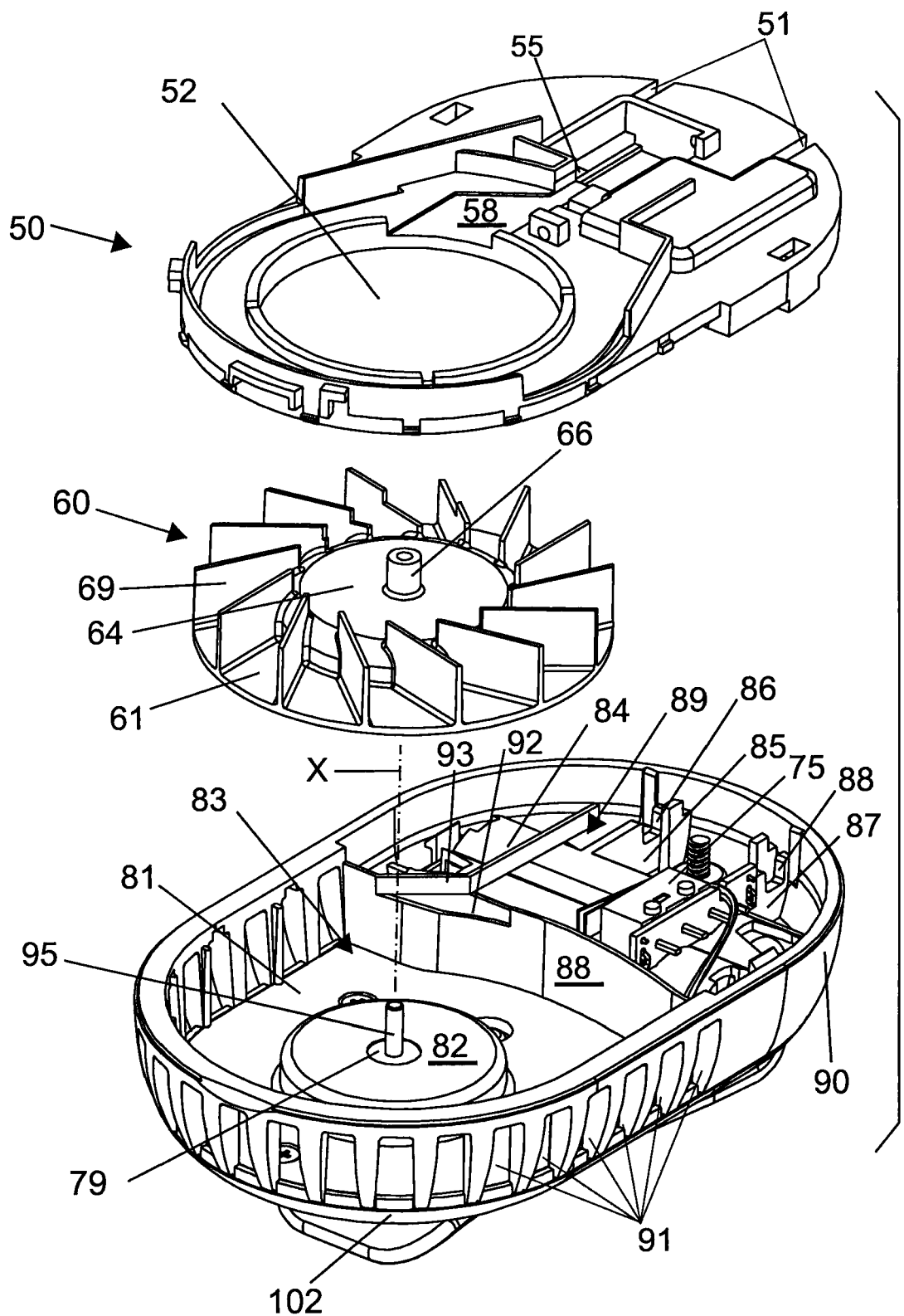
FIG. 3 is an exploded perspective view of specific components of the device of FIG. 1.
Figure 4:
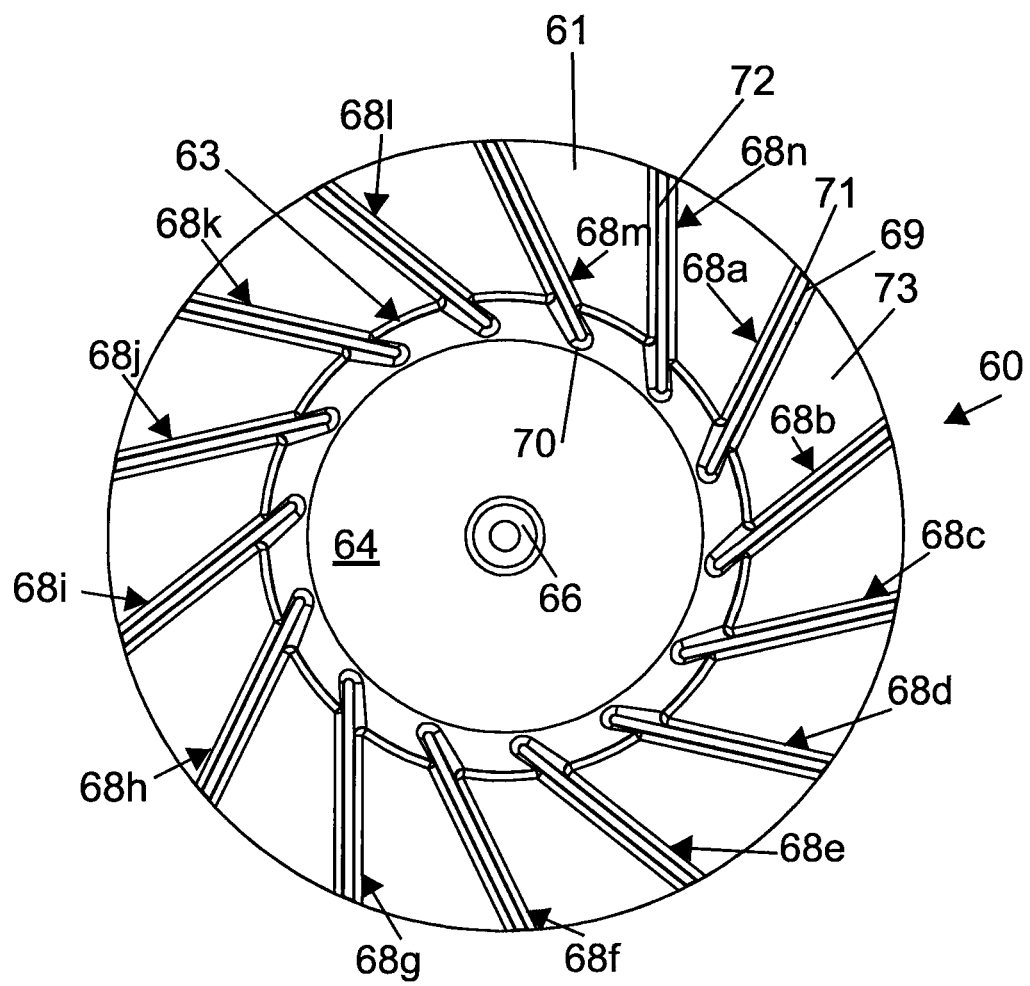
FIG. 4 is a top view of the rotor fan for use in the device of FIG. 1.
Figure 5:
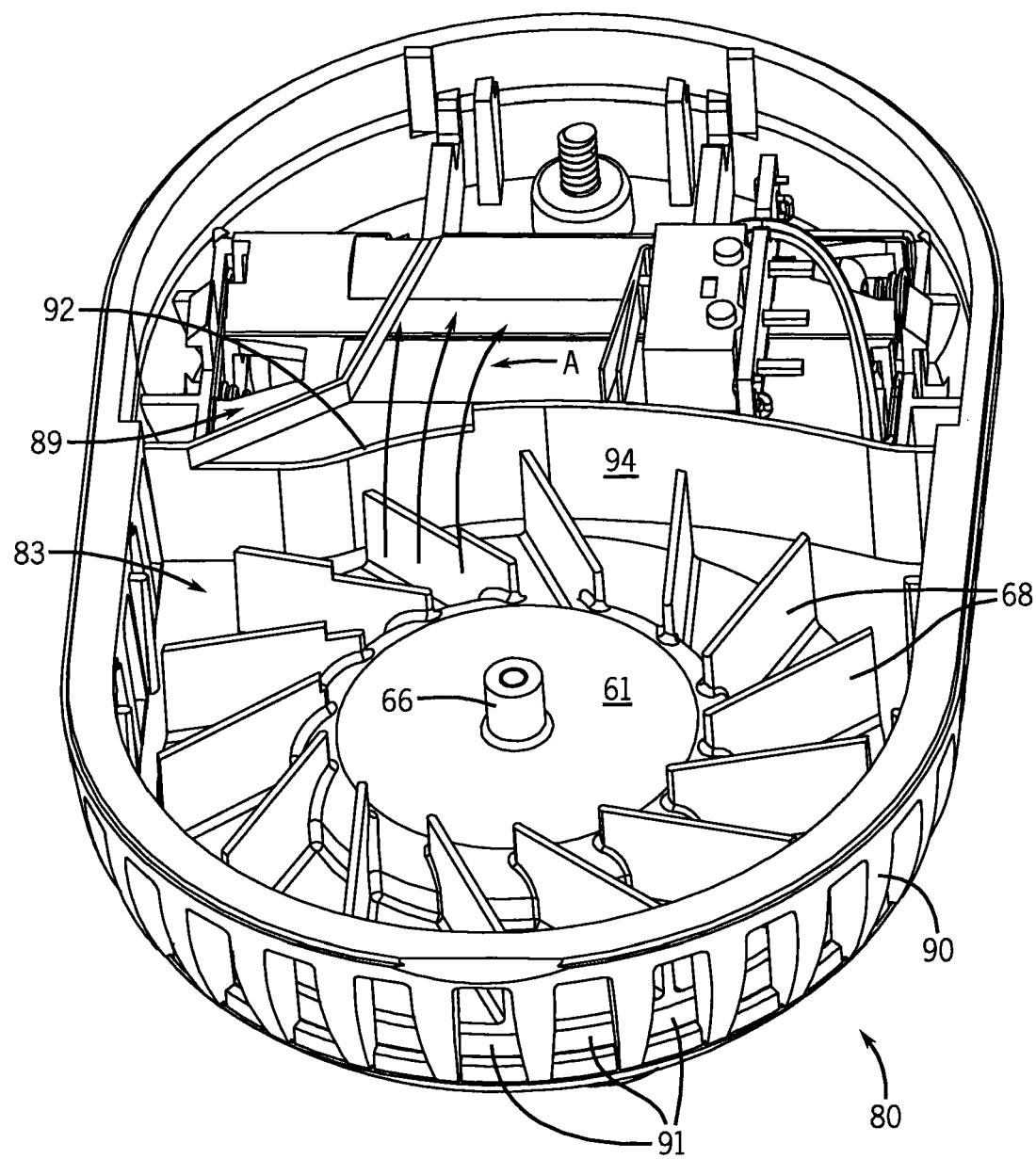
FIG. 5 is an enlarged perspective view of the housing of the device of FIG. 1 focusing on the flow path of air.
Figure 6:
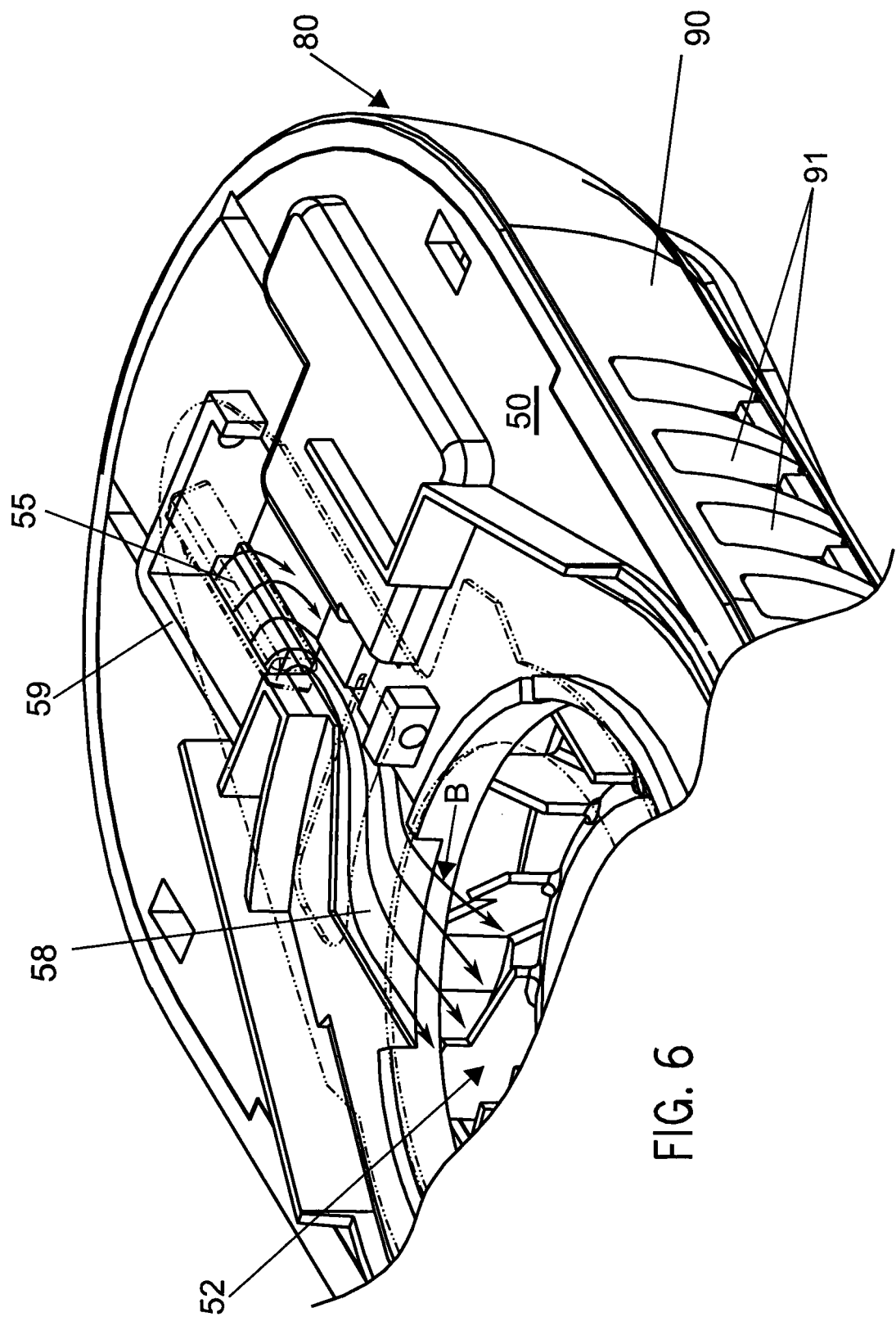
FIG. 6 is an enlarged perspective fragmentary view of a frame of the device of FIG. 1 focusing on the flow path of air.

Looking at FIGS. 3, 4, and 5, there is shown a fan 60 of the wearable chemical dispenser 18. The fan 60 has a rotor 61 having a central vertical wall 63 that joins a top central horizontal wall 64. The central vertical wall 63 and the top horizontal wall 64 define a recess (not shown) in the bottom of the rotor 61. The top horizontal wall 64 of the rotor 61 includes a tubular mounting element 66 on the axis of the rotor 61.

The preferred fan 60 includes fourteen fan blades 68a to 68n (see FIG. 4). It has been discovered that a fan configuration, which results in an ideal balance of airflow and minimal power consumption for the wearable chemical dispenser 18, includes twelve to eighteen fan blades. Preferably, the fan produces an average volumetric flow rate of air of 1.5 to 3 cubic feet per minute (with the refill cartridge 44 installed) over the life (e.g., at least eight, and most preferably at least twelve hours) of a refill cartridge 44. Typically, the fan will operate at 3000-5000 rpm. In one example wearable chemical dispenser 18, over the life (e.g., twelve hours) of a refill cartridge 44, the consumed power from the power supply is 0.35 watts or less, preferably 0.30 watts or less, more preferably 0.25 watts or less, and even more preferably 0.20 watts or less. In one example embodiment, over a twelve hour life of a refill cartridge 44, the consumed power from the power supply is about 0.17 watts while maintaining an average volumetric flow rate of air of at least 1.5 cubic feet per minute over the twelve hour period. When using one or more batteries for the power supply, the voltage will vary during discharge. However, the power consumed can be determined from the total energy consumed divided by the total time.

Each blade 68a to 68n has a generally rectangular body 69 defined by an inner edge 70, an outer edge 71, a top edge 72 extending from the inner edge 70 to the outer edge 71, and top surface 73 of the rotor 61.

It has been discovered that a fan configuration, which results in an ideal balance of airflow and minimal power consumption for the wearable chemical dispenser 18, includes a range of fan sizes and fan blade angles.

The wearable chemical dispenser 18 includes an electrical power supply. In the example embodiment shown, a microswitch 75 of the power supply is electrically connected to battery contacts (not shown). Another battery contact (not shown) completes an electrical circuit with batteries (not shown) and the battery contacts to provide electricity to the microswitch 75. When a user rotates the slide cover 28 by rotating the on-off button 29 into the 'on' position, the cam projection 32 of the slide cover 28 is driven into the rotating activation button 56 which then contacts the microswitch 75 to turn on the power supply.

Looking at FIG. 3, the wearable chemical dispenser 18 includes a main housing unit 80 for mounting various components of the wearable chemical dispenser 18. When the top housing section 20 and the main housing unit 80 are in a closed position (see, e.g., FIG. 1), a housing having an interior space is formed. The main housing unit 80 engages the frame 50 in a snap fit.

The main housing unit 80 has a bottom wall 81 with a raised portion 82 that defines a upwardly directed space (not shown) in the main housing unit 80. A battery compartment 84 is also provided in the bottom wall 81 of the main housing unit 80. The battery contacts are mounted at opposite ends of the battery compartment 84. Extending upward from the bottom wall 81 of the main housing unit 80 there is a hinge support 85 having a notch 86 and a hinge support 87 having a notch 88 (see FIG. 3). The hinge support 85 and the hinge support 87 form part of a hinge mechanism as described below.

The main housing unit 80 also includes a fan chamber 83 and a guide chamber 89, which are separated by a vertical wall 94. The vertical wall 94 includes a slot 92. The slot 92 allows air from the fan chamber 83 to enter the guide chamber 89. The guide chamber 89 is defined on one side by an internal rib 93.

The main housing unit 80 also includes a side wall 90 having regularly spaced openings 91 that define an outlet for permitting air mixed with air treatment chemical to exit the interior space of the wearable chemical dispenser 18. Together, the side wall 90 and the vertical wall 94 define the sides of the fan chamber 83.

In the non-limiting example embodiment shown in FIG. 2, the openings 91 in the side wall 90 extend from point E to point F around the side wall 90 of the main housing unit 80. In FIG. 5, the included angle between point E and point F and point D (which is on axis X shown in FIG. 3) is about 270 degrees. Therefore, the openings 91 are regularly spaced around 270 degrees of the side wall 90 of the main housing unit 80. Preferably, the openings 91 are regularly spaced around at least 180 degrees of the side wall 90 of the main housing unit 80. More preferably, the openings 91 are spaced around at least 235 degrees of the side wall 90 of the main housing unit 80. One non-limiting example of the total outlet area of the openings 91 is $8.5 \times 10^{-4}$ m². Advantageously, the battery compartment 84 is isolated from the openings 91. These example opening configurations contribute to an ideal balance of airflow and minimal power consumption for the wearable chemical dispenser 18.

Preferably, a flow path from the fan to the openings 91 is unobstructed. Some other devices included a slide cover designed to shut off air flow by blocking the inlet vents and the exhaust vents. The intent was to minimize loss of actives while the unit is not in use by blocking off airflow across the dosed pad. The walls blocking the exhaust vents and the geometries supporting them occupied large space and caused the device to increase in size. These blocking walls are eliminated in the present invention without increased loss in actives ingredient.

A motor 79 is positioned in the space (not shown) in the main housing unit 80 below the fan chamber 83, and a wire (not shown) connects the motor 79 to the microswitch 75 for powering the motor 79 when the rotating activation button 56 contacts the microswitch 75 to turn on the power supply. The fan 60 is positioned in the fan chamber 83 (See FIG. 5). The motor 79 includes a drive shaft 95 that is connected to the tubular mounting element 66 on the rotor 61. As a result, the motor 79 can rotate the fan 60. A battery door (not shown) covers the battery compartment in the bottom wall 81 of the main housing unit 80. The battery door includes mounting tabs (not shown). A bottom cover 102 is fastened to the main housing unit 80 by way of fasteners.

Turning now to FIGS. 5 and 6, the combination of the slot 92 in the vertical wall 94, internal rib 93, throughhole 55, sunken area 58, and vertical rib 59 create a flow path in which moving air from the fan chamber 83 can travel through the slot 92 into the guide chamber 89, through the throughhole 55 to an area below the useful life indicator 49.

As described in U.S. Patent Application Publication No. 2008/0141928 referred to above, a variety of chemicals can be used to provide a visual indicia of the extent of use by virtue of their disappearance or change. As the useful life indicator chemical, it is preferred to use a volatile liquid material that diffuses out of a shell, as described in that application. There is dye in the liquid so it can be easily seen when present. For example, one could use a dye like Fat Blue B 01 available from Clariant.

The useful life indicator 49 can be made of transparent polyethylene terephthalate. For the useful life indicator chemical it is most preferred to place a volatile solvent such as Norpar 12, a hydrocarbon from ExxonMobil Chemical Company in the useful life indicator 49, or to use that with a dye. Then, it is covered with a permeable layer such as an ultra low density polyethylene film (ULDPE) or a low density polyethylene film (LDPE). That is in turn covered before use by an impermeable peel-off layer, such as a peel-off layer or film having aluminum foil layer, preferably reinforced by an outer polyester layer. Immediately prior to use one can then peel off the peel-off layer, exposing the permeable layer at the back side of the useful life indicator 49.

When the device is on and the rotating activation button 56 is not covering the permeable layer, the fan 60 pushes air from the fan chamber 83 along flow path A through the slot 92 into the guide chamber 89. The air can then travel along flow path B through the throughhole 55, adjacent to the useful life indicator 49, through the sunken area 58, and back to the fan chamber 83. The air can then exit the wearable chemical dispenser 18 through the openings 91.

As the air moves past the useful life indicator 49, the volatile can slowly seep out of the useful life indicator 49, providing a visual cue as to the remaining useful life. As the consumer sees less color in the transparent window of the useful life indicator 49 they will know the status of the device's useful life (because absence of color means the device has reached the end of its useful life). Allowing air from the fan chamber to travel adjacent to the useful life indicator 49 helps coordinate the timing of the useful life indicator 49 with depletion of the air treatment chemical from the substrate 48.

When the device is off, the rotating activation button 56 essentially covers the back side of the useful life indicator 49, which avoids premature use up signals.

Looking now at FIGS. 1-3, the wearable chemical dispenser 18 includes a clip 110 for clipping the wearable chemical dispenser 18 to a user's clothing (e.g., a belt). The clip 110 can be rotated with respect to the wearable chemical dispenser 18.

Often a user will clip the wearable chemical dispenser 18 to a belt with the clip 110 of the wearable chemical dispenser 18 so that the outlet openings 91 face down from, to one side, and to the opposite side of the user. This directs a mixture of air and air treatment chemical down from, to one side, and to the opposite side of the user. If a user wishes to direct the mixture of air and air treatment chemical up, down, and to one side, the user can rotate the housing the rotating clip 110 as described above. A user may also wish to rotate the housing in order to avoid any pinching against the body when sitting. Also, by locating a pivot point of the clip 110 in a section of the housing adjacent the outlet openings 91, more precise control of the direction of the mixture of air and air treatment chemical is afforded when rotating the clip 110. Thus, the housing of the wearable chemical dispenser 18 can be vertical or horizontal when in use.

Regarding component construction, the top housing section 20, slide cover 28, hinge bracket 36, support structure 45 of the refill cartridge 44, frame 50, fan 60, main housing unit 80, battery door 96, bottom cover 102, and clip 110 may be formed from a suitable polymeric material such as polyethylene, polypropylene, or polyester.

In operation, the wearable chemical dispenser 18 will be clipped on a belt, purse or the like using clip 110 for that purpose. When a user moves the on-off button 29 along the side wall 22 of the top housing section 20 into the 'on' position, the openings 31 of the slide cover 28 align with the apertures 24 that are radially arranged in the top wall 23 of the top housing section 20. The cam projection 32 of the slide cover 28 is driven into the rotating activation button 56 which then contacts the microswitch 75 to turn on the power supply to power the fan 60 by way of motor 79. Air is sucked by the fan 60 of the wearable chemical dispenser 18 in through apertures 24 and the openings 31. As the air passes through fabric substrate 48, the air treatment chemical mixes into the air and a mixture of air and air treatment chemical is then blown radially out openings 91 (preferably down along pants or dresses). A user can rotate the clip 110 as described above.

While the present device is primarily intended to be used as a wearable item carried with a human when outdoors, it can also be laid flat, with the clip 110 downward and the top housing section 20 upward, on a picnic table or the like. When used in this manner it can provide protection to an area during a picnic or similar outdoor activity.

Hence, the device is much more compact and lightweight, yet still effective. Further, the cost of operation from a battery standpoint is reduced. The device can more comfortably be used when seated, and provides greater control over dispensing direction. Also, installing a replacement active refill is easier. Additionally, depletion of the useful life indicator is better correlated to depletion of the air treatment chemical from the substrate. These advantages are achieved at lowered cost, and provide a reliable construction.

In the wearable dispenser, the intake grill size is designed to work in concert with an improved fan which falls within a specific range of fan blades, size and blade angle. A low current draw motor is recessed into the axial hub of the fan design. The airflow exits through 270 of output vents. This combination of design features results in an ideal balance of airflow and minimal power consumption that results in a highly efficient system, which produces good insect repellency and usage duration in a relatively small, lightweight unit.

While an example embodiment has been described above, it should be appreciated that there are numerous other embodiments of the invention within the spirit and scope of this disclosure. For example, the device can be powered by a different source of energy (e.g. a solar power panel), other forms of actives can be dispensed along with or in substitution for the insect control ingredients (e.g. a fragrance or deodorizing chemical), and even when an insect control ingredient is dispensed it need not be one focused on controlling mosquitoes (e.g. chemicals for repelling other flying or crawling insects or pests can be used). Hence, the invention is not to be limited to just the specific embodiments shown or described.

INDUSTRIAL APPLICABILITY

Provided herein are wearable dispensing devices capable of dispensing insect control chemicals and/or other air treatment chemicals adjacent a human body.

What is claimed is:

1. A wearable device for dispensing an air treatment chemical, the device comprising:
   a main housing unit including an inlet for permitting air to enter into an interior space of the housing, an outlet for permitting air mixed with an air treatment chemical to exit the interior space, a fan chamber, a guide chamber, and a slot between the fan chamber and the guide chamber;
   a cartridge positioned in the housing, the cartridge including a substrate bearing an air treatment chemical and a useful life indicator;
   a frame positioned in the housing, the frame having a throughhole adjacent to the guide chamber;
   a power supply mounted in the housing;
   a motor mounted in the housing, the motor being powered by the power supply; and
   a fan mounted in the fan chamber, the fan being capable of moving air from the inlet adjacent to the substrate so as to mix air treatment chemical into the moving air, and then deliver a mixture of air and air treatment chemical through the outlet to an outside of the housing,
   wherein the slot, guide chamber, and throughhole define a flow path for the moving air to flow adjacent to the useful life indicator.

2. The wearable device of claim 1 wherein the device further comprises a switch for turning the fan on and off.

3. The wearable device of claim 1 wherein the useful life indicator changes appearance by evaporation of a material.

4. The wearable device of claim 1 wherein the flow path directs the moving air under the useful life indicator.

5. The wearable device of claim 1 wherein the frame further includes a sunken area between the slot and the fan chamber.

6. The wearable device of claim 5 wherein the sunken area directs the moving air from the useful life indicator to the housing outlet.

7. The wearable device of claim 1 further comprising a movable slide cover that blocks air flow when in a first, closed position and allows the air to flow when in a second, open position, the slide cover having a projection thereon that interacts with a switch so that moving the slide cover to the second, open position activates the switch to turn on the fan.

8. The wearable device of claim 7 further comprising a rotating activation button that must be rotated by interaction with the projection of the slide cover before the switch can be activated.

9. The wearable device of claim 8 wherein the rotating activation button, as it is rotated by interaction with the projection of the slide cover as the slide cover is moved, moves from a position inhibiting the evaporation of material from the useful life indicator to a second position wherein evaporation of material from the useful life indicator is readily permitted.

10. The wearable device of claim 8 wherein the rotating activation button is located adjacent to the slot.

11. The wearable device of claim 1 wherein the fan chamber is defined by a vertical wall.

12. The wearable device of claim 11 wherein the fan chamber and the guide chamber are separated by the vertical wall.

13. The wearable device of claim 12 wherein the slot is located in the top edge of the vertical wall.

14. The wearable device of claim 12 wherein the frame contacts a top edge of the vertical wall.

15. The wearable device of claim 14 wherein a top of the guide chamber is defined by the frame.

16. The wearable device of claim 15 wherein the throughhole defines a portion of the top of the guide chamber.

17. The wearable device of claim 16 wherein the throughhole is the sole outlet for airflow from the guide chamber.

18. The wearable device of claim 1 wherein the slot is the sole inlet for airflow into the guide chamber.

19. The wearable device of claim 12 wherein the guide chamber includes an internal rib extending from the vertical wall.

20. The wearable device of claim 1 wherein the frame includes a vertical rib to ensure air flow adjacent to the useful life indicator.

21. A method of indicating a remaining amount of useful life of an air treatment chemical being dispensed by a wearable device, the method comprising:
   A. providing the wearable device having:
      (i) a main housing unit including an inlet for permitting air to enter into an interior space of the housing, an outlet for permitting air mixed with an air treatment chemical to exit the interior space;
      (ii) a cartridge positioned in the main housing unit, the cartridge including a substrate bearing an air treatment chemical and the useful life indicator;
      (iii) a frame positioned in the main housing unit;
      (iv) a power supply mounted in the main housing unit;
      (v) a motor mounted in the main housing unit, the motor being powered by the power supply;
      (vi) a fan capable of moving air from the inlet adjacent to the substrate so as to mix air treatment chemical into the moving air, and then deliver a mixture of air and air treatment chemical through the outlet to an outside of the main housing unit;
B. providing a flow path for the moving air to flow adjacent to the useful life indicator; and
C. directing the moving air through the flow path at useful life indicator; wherein the moving air flows past the underside of the useful life indicator.

22. The method of claim 21 wherein the main housing unit includes a fan chamber, a guide chamber, and a slot between the fan chamber and the guide chamber and the frame includes throughhole adjacent to the guide chamber, wherein the fan chamber, guide chamber, slot, and throughhole define the flow path and wherein the moving air flows along an underside of the useful life indicator.

\* \* \* \* \*